United States Patent
Perryman et al.

(10) Patent No.: US 12,285,618 B2
(45) Date of Patent: Apr. 29, 2025

(54) HEADSETS FOR POSITIONING ELECTRONIC DEVICES

(71) Applicant: Curonix LLC

(72) Inventors: Laura Tyler Perryman, Pompano Beach, FL (US); Chad David Andresen, Miami Beach, FL (US)

(73) Assignee: CURONIX LLC, Pompano Beach, FL (US)

( * ) Notice: Subject to any disclaimer, the term of this patent is extended or adjusted under 35 U.S.C. 154(b) by 0 days.

(21) Appl. No.: 18/139,331

(22) Filed: Apr. 25, 2023

(65) Prior Publication Data

US 2023/0330423 A1    Oct. 19, 2023

Related U.S. Application Data

(63) Continuation of application No. 16/691,863, filed on Nov. 22, 2019, now Pat. No. 11,672,990.

(60) Provisional application No. 62/792,498, filed on Jan. 15, 2019.

(51) Int. Cl.
| | |
|---|---|
| *A61N 1/37* | (2006.01) |
| *A42B 1/22* | (2006.01) |
| *A42B 1/245* | (2021.01) |
| *A61N 1/372* | (2006.01) |
| *A61N 1/375* | (2006.01) |
| *A61N 1/36* | (2006.01) |

(52) U.S. Cl.
CPC ............ *A61N 1/37229* (2013.01); *A42B 1/22* (2013.01); *A42B 1/245* (2013.01); *A61N 1/375* (2013.01); *A61N 1/36071* (2013.01); *A61N 1/36075* (2013.01); *A61N 1/372* (2013.01)

(58) Field of Classification Search
CPC ............................ A61N 1/37229; A61N 1/375
See application file for complete search history.

(56) References Cited

U.S. PATENT DOCUMENTS

| | | | |
|---|---|---|---|
| 8,682,452 B2 * | 3/2014 | Minogue | A61N 1/36014 607/139 |
| 10,687,138 B2 * | 6/2020 | Mainini | H04R 3/12 |
| 11,672,990 B2 * | 6/2023 | Perryman | A61N 1/375 607/46 |
| 2005/0004619 A1 * | 1/2005 | Wahlstrand | A61N 1/3787 607/45 |
| 2005/0064918 A1 * | 3/2005 | Medhin | H04M 1/05 455/575.2 |

(Continued)

FOREIGN PATENT DOCUMENTS

| | | |
|---|---|---|
| JP | 5748939 | 7/2015 |
| WO | WO 2012/138782 | 10/2012 |

(Continued)

*Primary Examiner* — Eric D. Bertram
(74) *Attorney, Agent, or Firm* — Maschoff Brennan

(57) ABSTRACT

A headset for positioning an electronic device against a head of a patient includes a flexible frame configured to surround a portion of the head, the flexible frame defining an interior channel and an exterior slot, a curved structure configured to grasp an ear of the patient, the curved structure being movable within the interior channel of the flexible frame for accommodating a size of the head, and a mount including a support base to which the electronic device can be attached, the mount being slidable along the exterior slot of the flexible frame to position the electronic device along the head.

20 Claims, 8 Drawing Sheets

(56) References Cited

U.S. PATENT DOCUMENTS

| | | | |
|---|---|---|---|
| 2009/0052718 A1* | 2/2009 | Ito | H04R 1/1066 |
| | | | 381/380 |
| 2009/0082835 A1 | 3/2009 | Jaax et al. | |
| 2010/0010565 A1 | 1/2010 | Lichtenstein | |
| 2010/0046782 A1 | 2/2010 | Ito et al. | |
| 2010/0189303 A1* | 7/2010 | Danielson | H04R 1/1008 |
| | | | 381/378 |
| 2018/0147412 A1* | 5/2018 | Oh | A61N 1/36038 |
| 2019/0009097 A1* | 1/2019 | Hartley | H02J 50/90 |
| 2019/0222911 A1* | 7/2019 | Alwicker | H04R 1/1008 |
| 2023/0330423 A1* | 10/2023 | Perryman | A61N 1/37229 |

FOREIGN PATENT DOCUMENTS

| | | |
|---|---|---|
| WO | WO 2013/019757 | 2/2013 |
| WO | WO 2013/025632 | 2/2013 |
| WO | WO 2013/040549 | 3/2013 |
| WO | WO 2012/103519 | 3/2014 |

\* cited by examiner

HEADSETS FOR POSITIONING ELECTRONIC DEVICES

CROSS-REFERENCE TO RELATED APPLICATION

This application is a continuation of, and claims priority to, U.S. application Ser. No. 16/691,863, filed Nov. 22, 2019, now U.S. Pat. No. 11,672,990, which claims the benefit of U.S. Provisional Application No. 62/792,498, filed Jan. 15, 2019, and titled "Headsets for Positioning Electronic Devices." The disclosure of each of the foregoing applications is incorporated herein by reference in their entirety.

TECHNICAL FIELD

This disclosure relates to headsets for positioning an antenna against a head of a patient so that the antenna can communicate with a tissue stimulator implanted within the head.

BACKGROUND

Modulation of tissue within the body by electrical stimulation has become an important type of therapy for treating chronic, disabling conditions, such as chronic pain, problems of movement initiation and control, involuntary movements, dystonia, urinary and fecal incontinence, sexual difficulties, vascular insufficiency, and heart arrhythmia. For example, an external antenna can be used to send electrical energy to electrodes on an implanted tissue stimulator that can pass pulsatile electrical currents of controllable frequency, pulse width, and amplitudes to a tissue. In order to deliver a desired therapy to the tissue, the external antenna should be optimally positioned along a skin surface of the body with respect to the tissue stimulator in a secure manner.

SUMMARY

In general, this disclosure relates to headsets for positioning an antenna against a head of a patient so that the antenna can communicate with a tissue stimulator implanted within the head.

In one aspect, a headset for positioning an electronic device against a head of a patient includes a flexible frame configured to surround a portion of the head, the flexible frame defining an interior channel and an exterior slot, a curved structure configured to grasp an ear of the patient, the curved structure being movable within the interior channel of the flexible frame for accommodating a size of the head, and a mount including a support base to which the electronic device can be attached, the mount being slidable along the exterior slot of the flexible frame to position the electronic device along the head.

Embodiments may provide one or more of the following features.

In some embodiments, the flexible frame has a thickness of about 0.3 cm to about 0.5 cm.

In some embodiments, the portion of the head includes a base of the head.

In some embodiments, the flexible frame includes one or more of acrylonitrile butadiene styrene, rubber, silicone, polyvinyl chloride, and thermoplastics.

In some embodiments, the headset is configured such that the curved structure extends from the flexible frame underneath the ear to wrap around the ear.

In some embodiments, the headset is configured such that the curved structure extends from the flexible frame above the ear to wrap around the ear.

In some embodiments, the curved structure is coupled to the flexible frame in a telescopic arrangement.

In some embodiments, a position of the curved structure relative to the flexible frame is securable via a friction fit.

In some embodiments, the curved structure is a first curved structure, and the headset further includes a second curved structure configured to grasp the other ear of the patient.

In some embodiments, a position of the mount relative to the flexible frame is securable via a friction fit.

In some embodiments, a position of the mount relative to the flexible frame is securable via a mechanical fastener.

In some embodiments, the mount further includes a connector from which the support base extends, and wherein the connector at least partially surrounds the flexible frame.

In some embodiments, the support base is arranged to position the electronic device against the base of the head.

In some embodiments, the support base is configured to compress the electronic device against the head.

In some embodiments, the mount is oriented at an angle of about 26.1 degrees to about 26.9 degrees with respect to the flexible frame.

In some embodiments, the mount includes one or more of acrylonitrile butadiene styrene, rubber, silicone, polyvinyl chloride, and thermoplastics.

In some embodiments, the mount includes a first mechanical fastener to which a second mechanical fastener on the electronic device can be attached to secure the electronic device to the mount.

In some embodiments, the mount includes a hook material section to which a loop material section on the electronic device can be attached to secure the electronic device to the mount.

In some embodiments, the electronic device includes an antenna that is configured to communicate with a tissue stimulator implanted within the head.

In some embodiments, the headset has a weight in a range of about 5 g to about 60 g.

DETAILED DESCRIPTION

Figure 1:
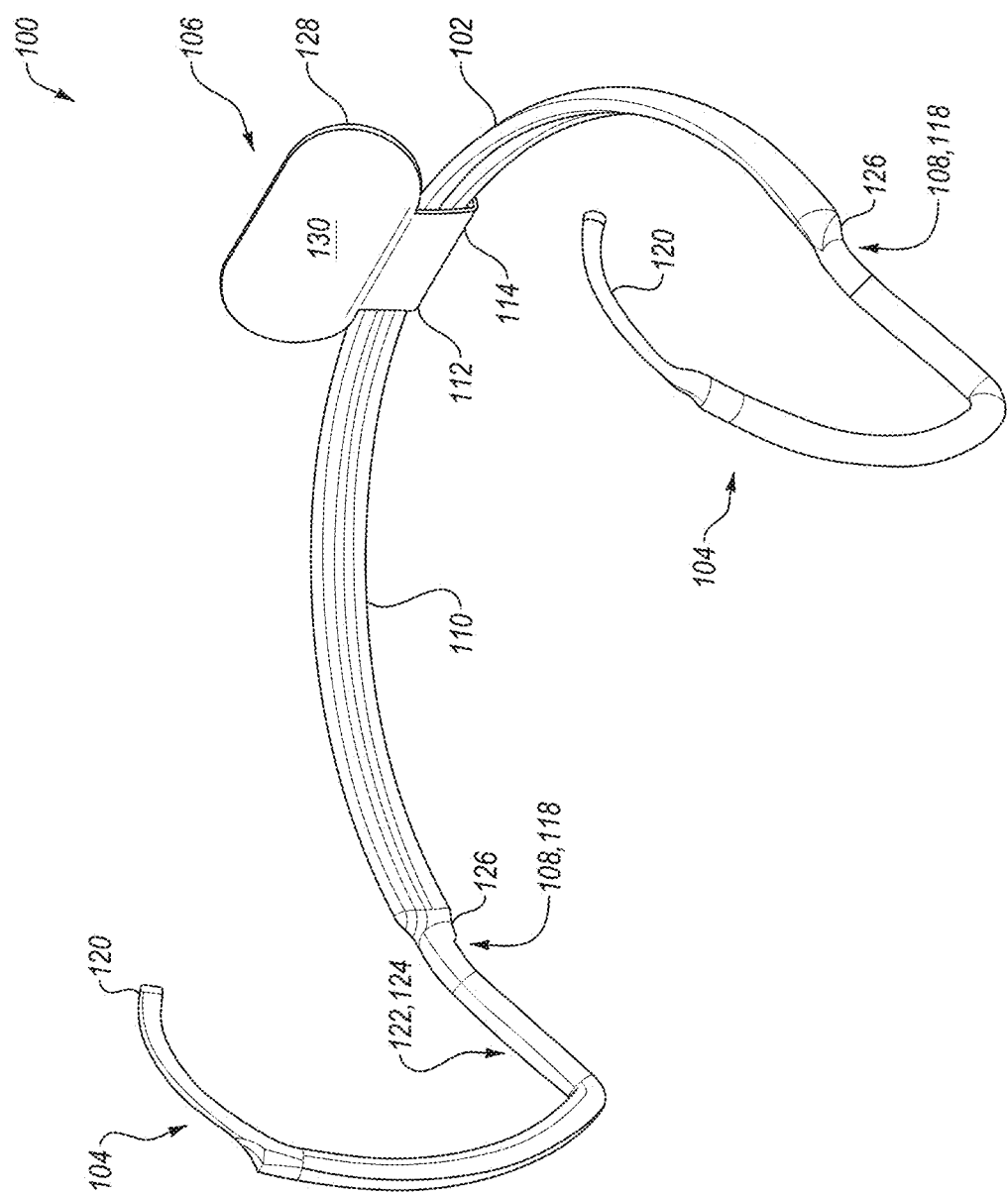
FIG. 1 is a perspective view of a headset for positioning an antenna against a head of a patient.

FIGS. 1-4 illustrate a headset 100 that can be used to position an antenna against the head 101 of a patient for communicating with a wireless tissue stimulator implanted within the patient's head. The tissue stimulator can deliver electrical therapy to tissues within the patient's head to treat conditions such as migraine headaches, face pain, and craniofacial peripheral neuropathy. The headset 100 is a lightweight, molded component that is designed to be comfortably secured to the patient's head. The headset 100 includes a central frame 102, two curved fixtures 104 extending from opposite front ends 118 of the central frame 102, and a mount 106 that is movable along the central frame 102.

The central frame 102 is provided as a curved, elongate structure that is formed to surround and seat against a base 103 of the patient's head 101. The central frame 102 defines an interior channel 108 in which the curved fixtures 104 can slide and an exterior slot 110 along which the mount 106 can slide for desired positioning with respect to the tissue stimulator implanted within the patient's head 101.

Figure 2:
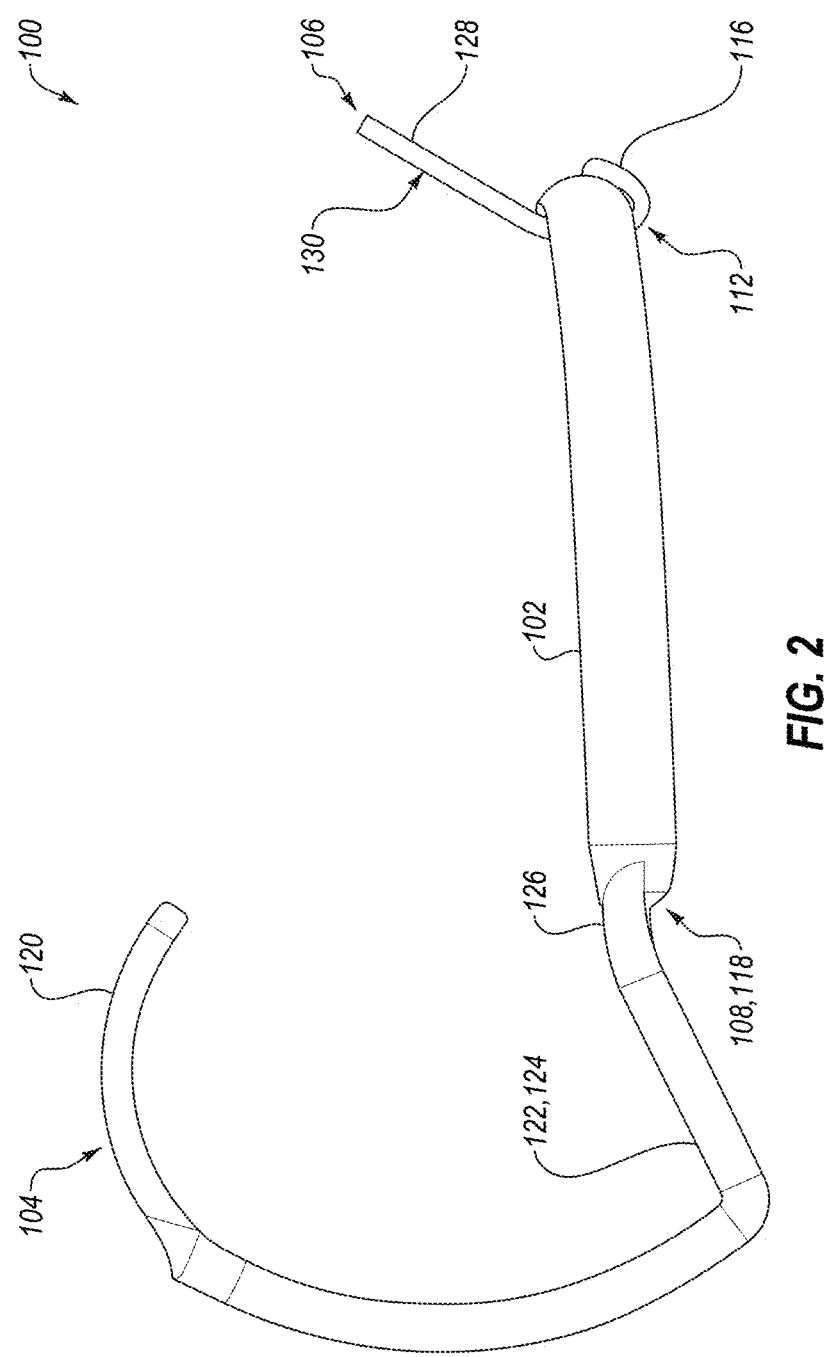
FIG. 2 is a side view of the headset of FIG. 1.
Figure 3:
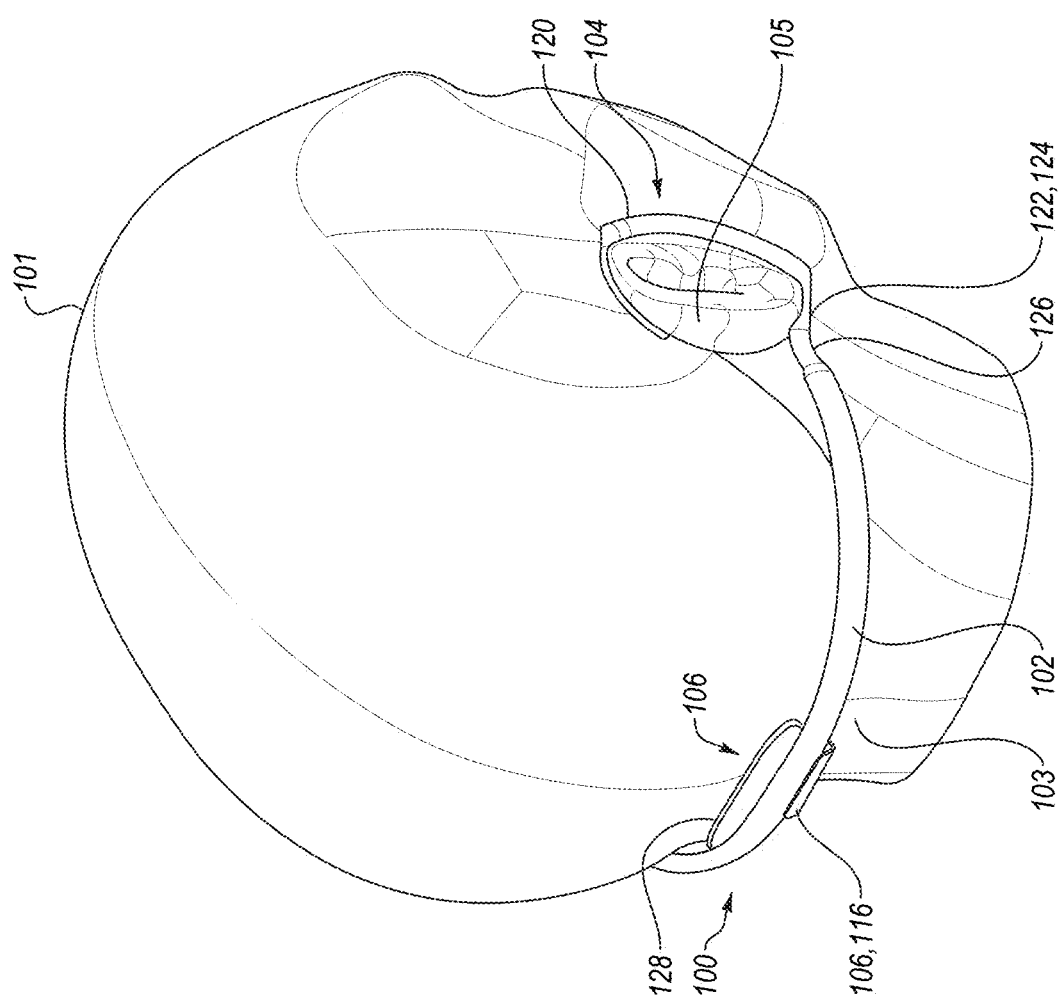
FIG. 3 is a perspective view of the headset of FIG. 1 while secured to a head of a patient.
Figure 4:
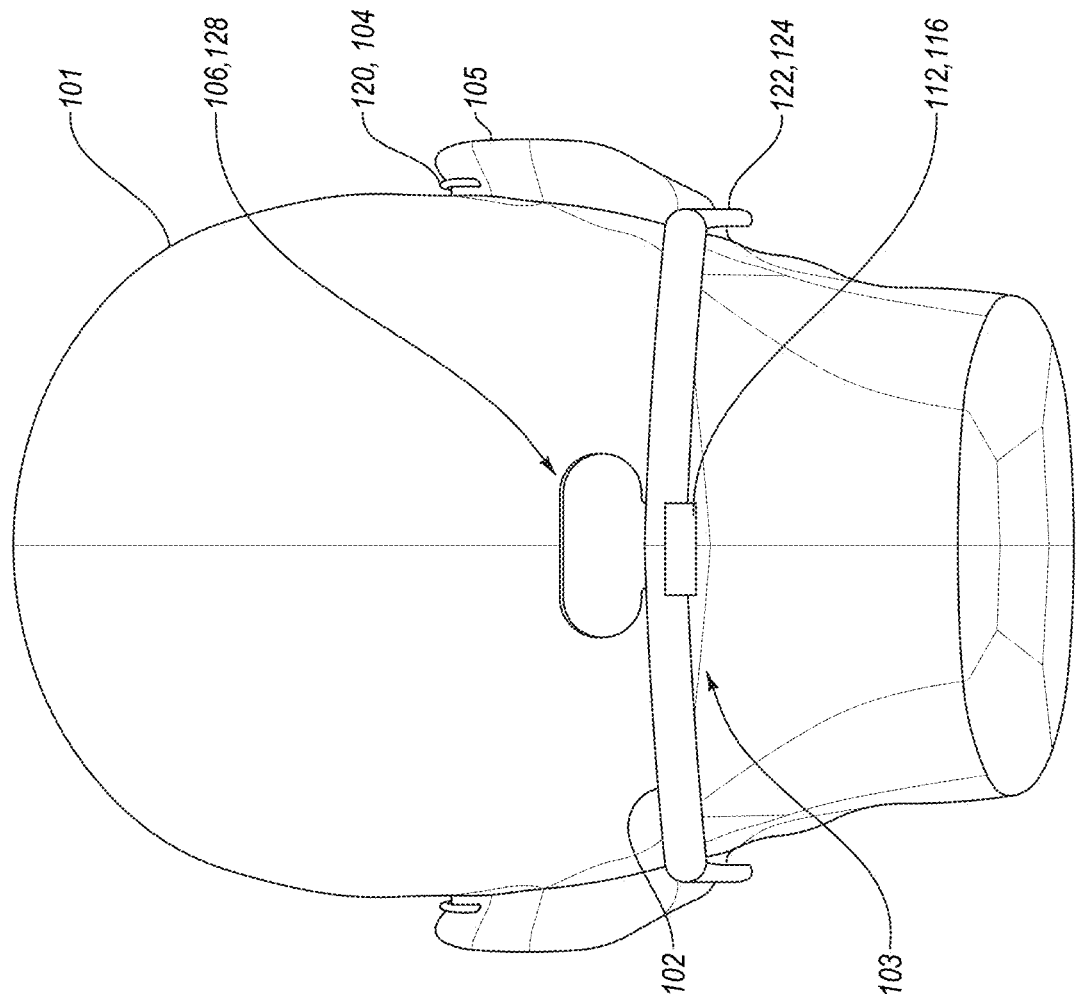
FIG. 4 is a rear view of the headset of FIG. 1 while secured to a head of a patient.

The curved fixtures 104 are formed to grasp the patient's ears 105 to snuggly secure the headset 100 to the patient's head 101. Each curved fixture 104 includes a hook 120 and a shaft 122. The hooks 120 of the curved fixtures 104 can be wrapped around a front edge of the patient's ears 105 to a rear edge of the patient's ears 105, as shown in FIGS. 3 and 4. Accordingly, the curved fixtures 104 are designed to distribute a load around the ears 105. Each shaft 122 includes an exposed end region 124 and an extension piece 126 that is disposed within the interior channel 108 of the central frame 102. The extension pieces 126 of the shafts 122 (e.g., shown in a fully retracted configuration in FIGS. 1 and 2) can slide telescopically in and out of the interior channel 108 of the central frame 102 to adjust an effective size (e.g., a length and a circumference) of the headset 100 for comfortably accommodating a size of the patient's head 101. A position of the curved fixtures 104 relative to the central frame 102 can be maintained by tension due to the elastic properties of the selected materials between the extension pieces 126 of the shafts 122 and the central frame 102.

The mount 106 is designed to stably support the antenna to position the antenna against a skin surface along the base 103 of the patient's head 101. The mount 106 includes a connector 112 with a flange 114 that engages the exterior slot 110 and a hook 116 that wraps around an outer surface of the central frame 102. The flange 114 can slide along the central frame 102 within the exterior slot 110 and can maintain the mount 106 in a desired position along the exterior slot 110 via a friction fit between the mount 106 and the central frame 102. The hook 116 stabilizes an orientation of the mount 106 by preventing the mount 106 from rotating away from the exterior slot 110. The mount 106 further includes a support base 128 that extends upward from the connector 112. The support base 128 is provided is a thin plate and includes an inner surface 130 to which the antenna can be secured for positioning the antenna against the patient's head 101.

Figure 6:
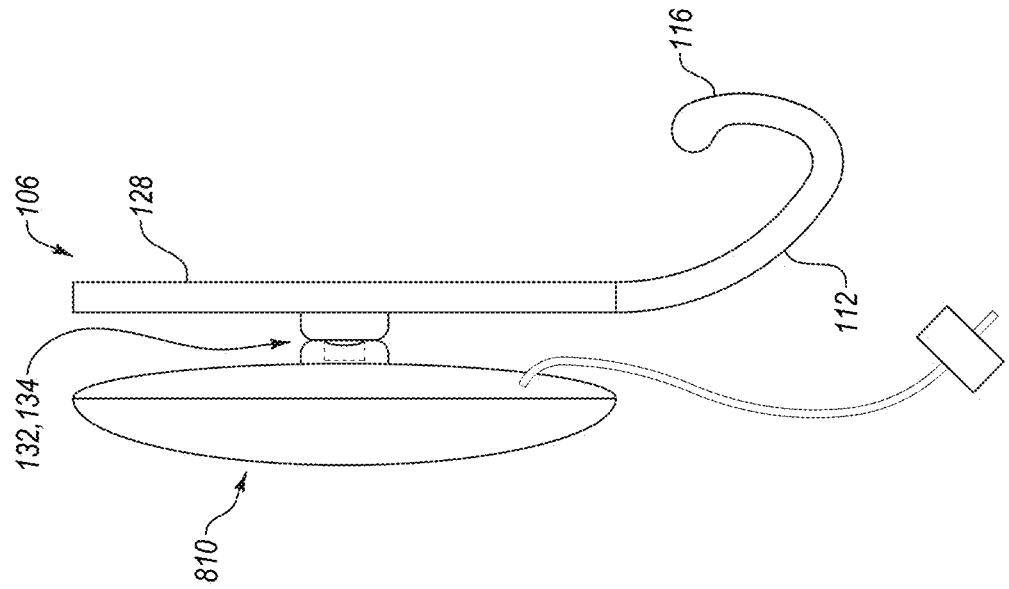
FIG. 6 is side view of the mount of FIG. 5 attached to the antenna at the snap fixture.
Figure 5:
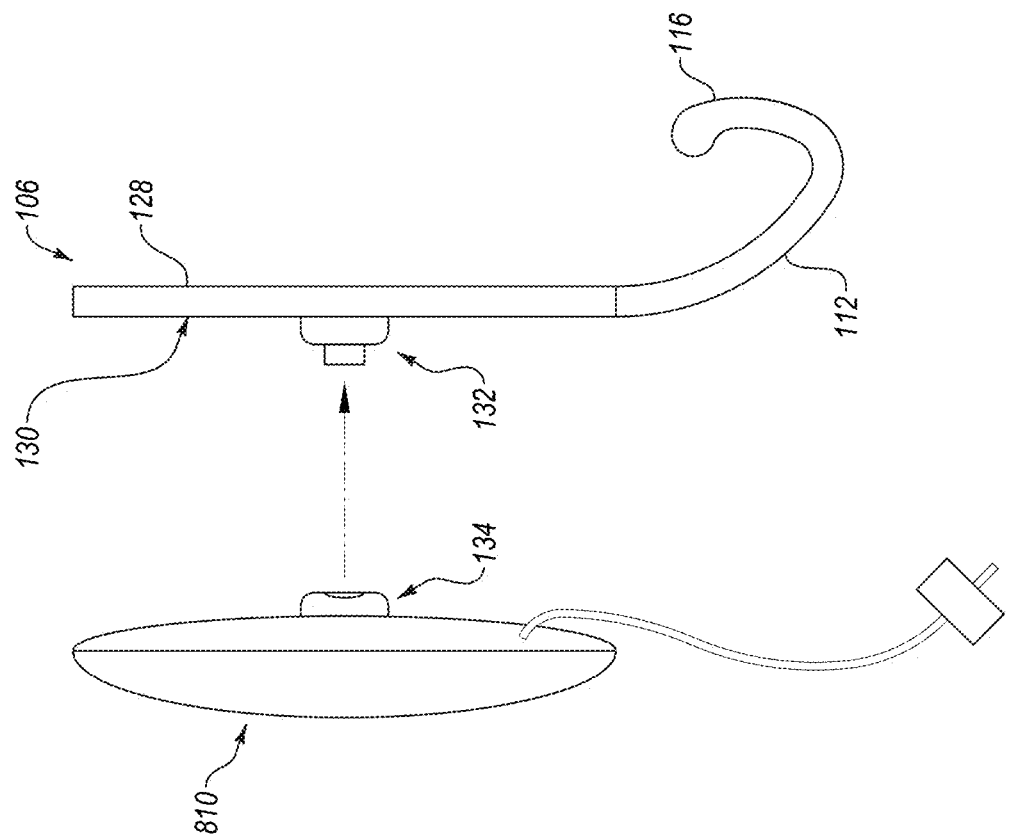
FIG. 5 is a side view of a mount of the headset of FIG. 1, including a snap fixture for attachment to an antenna.
Figure 7:
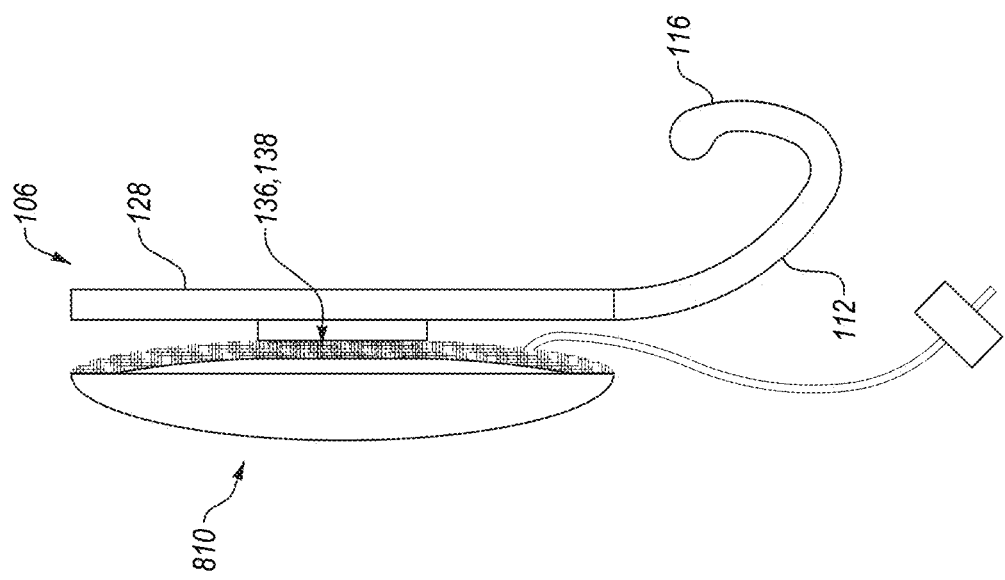
FIG. 7 is a side view of a mount of the headset of FIG. 1, including a strip of hook material for attachment to an antenna.
Figure 8:
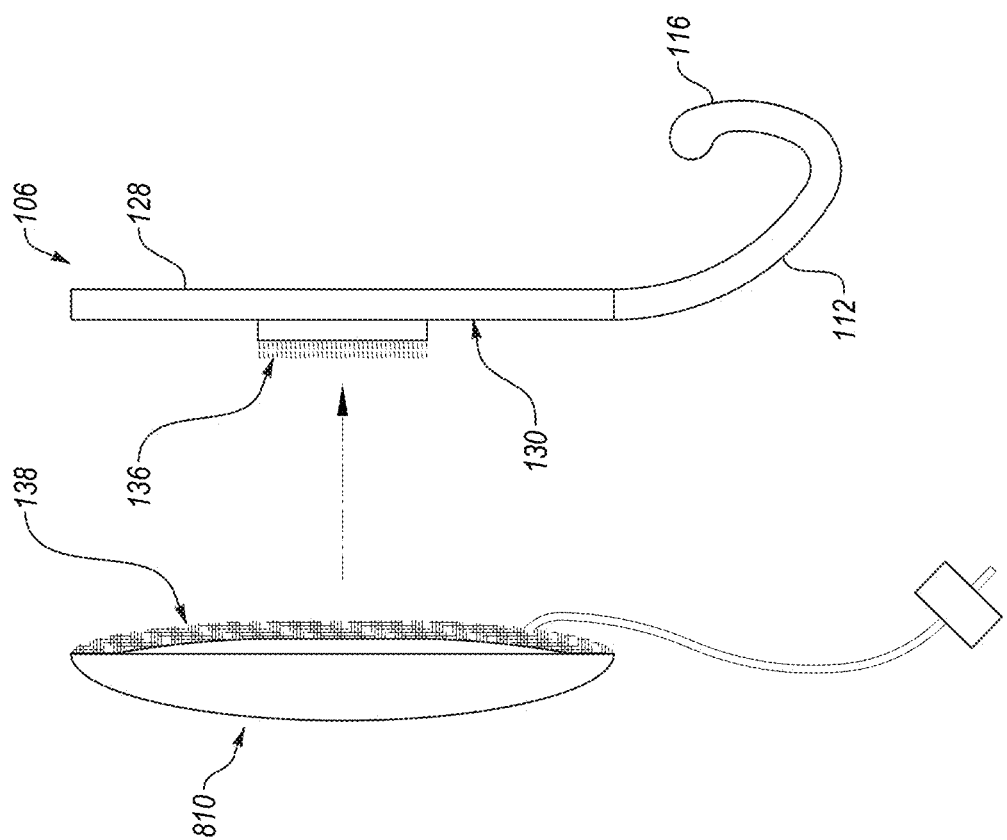
FIG. 8 is side view of the mount of FIG. 6, with the strip of hook material attached to a strip of loop material along the antenna.

For example, as shown in FIGS. 5 and 6, the support base 128 may be equipped with a snap closure 132 by which an antenna 810 can be attached to the mount 106 at a mating snap closure 134 disposed on the antenna 810. Referring to FIGS. 7 and 8, in some embodiments, the support base 128 may be equipped with a strip of hook material 136 by which an antenna 810 can be attached to the mount 106 at a mating strip of loop material 138 disposed on the antenna 810. In some embodiments, the support base 128 may be equipped with a strip of loop material, and the antenna 810 may be equipped with a mating strip of hook material.

Referring again to FIGS. 1-4, in a resting configuration of the headset 101 (e.g., unattached to a patient's head, as shown in FIGS. 1 and 2), the central frame 102 typically has an inner width (e.g., in a direction extending from a left side of the head 101 to a right side of the head 101) of about 11.4 cm to about 13.5 cm and an inner depth (e.g., extending from the front ends 118 to the rear edge) of about 5.7 cm to about 6.7 cm. The central frame 102 typically has a total thickness of about 0.3 cm to about 0.5 cm, providing the headset 101 with a low profile that is radially close to the head 101 to minimize visibility of the headset 101.

The hooks 120 of the curved fixtures 104 (e.g., from the exposed end regions 124 of the shafts 122) typically have a total height of about 3.6 cm to about 4.3 cm. The hooks 120 typically have a front to rear total width of about 0.3 cm to about 0.5 cm. The exposed end regions 124 of the shafts 122 typically have a length of about 1.9 cm to about 2.3 cm, and the extension pieces 126 of the shafts 122 typically have a length of about 0.7 cm to about 0.9 cm. Referring particularly to FIG. 2, the exposed end regions 124 are typically oriented at an angle of about 26.1 degrees to about 26.9 degrees from the extension pieces 126 to wrap underneath the patient's ears 105 (as shown in FIGS. 3 and 4). Owing to the telescopic arrangement of the shafts 122 within the central frame 102, the headset 100 can typically be adjusted in size to accommodate heads 101 that have a diameter in a range of about 10.8 cm to about 15.6 cm.

The support base 128 of the mount 106 typically has a length of about 3.3 cm to about 3.4 cm, a width of about 1.6 cm to about 1.7 cm, and a thickness of about 0.11 cm to about 0.15 cm. Referring particularly to FIG. 2, the support base 128 is typically oriented at an angle of about 28 degrees to about 32 degrees from the connector 112 (e.g., and from therefore from the central frame 102) in order to accommodate a natural shape or curvature of the patient's head 101. The support base 128 can apply a mild compressive force to the patient's head 101 to securely hold the antenna in place against the patient's head 101.

The central frame 102, the curved fixtures 104, and the mount 106 are typically made of one or more materials that provide the headset 100 with enough rigidity to stably support the antenna and surround a rear portion of the head 101, that provide the headset 100 with enough malleability and flexibility to allow the headset 100 to stretch and bend to accommodate heads 101 of different sizes and shapes, and that are soft enough to provide a comfortable contact surface for the head 101. Example materials from which the central frame 102 and the curved fixtures 104 may be made include acrylonitrile butadiene styrene (ABS), rubber, silicone, polyvinyl chloride (PVC), and thermoplastics. Such materials may have an elastic modulus in a range of about $0.1 \times 10^9$ Pa to about $80 \times 10^9$ Pa and a durometer in a range of 20 A to 90 D. Example materials from which the mount 106 may be made include acrylonitrile butadiene styrene (ABS), rubber silicone, PVC, and thermoplastics. Such materials may have an elastic modulus in a range of about $0.1 \times 10^9$ Pa to about $80 \times 10^9$ Pa and a durometer in a range of 20 A to 90 D. In some embodiments, the components of the headset 100 are made of a relatively hard, rigid core material that is surrounded by a relatively soft, flexible outer material for contacting the patient's head 101. The components of the headset 100 are typically manufactured via injection molding, 3D printing or CNC machining.

The headset 100 has a light weight that is typically in a range of about 5 g to about 60 g to maximize patient comfort, as pressure applied to a patient's head 101 can often trigger pain. The headset 100 also minimizes pressure to the patient's head 101 in that the headset 100 only partially surrounds the head 101, as opposed to fully surrounding the head 101 (e.g., along a patient's forehead). The various smooth, rounded edges along the headset 100 also contribute to patient comfort.

While the headset 100 has been described and illustrated as including certain dimensions, sizes, shapes, materials, arrangements, and configurations, in some embodiments, headsets that are similar in structure and function to the headset 100 may include different dimensions, sizes, shapes, materials, arrangements, or configurations.

For example, while mount 106 and the central frame 102 have been described and illustrated as being positioned with respect to each other via friction fit, in some embodiments, a headset that is otherwise similar in structure and function to the headset 100 may include a set screw for locking a position of the mount 106 with respect to the central frame 102.

While the curved fixtures 104 have been described and illustrated as having an under the ear configuration, in some embodiments, a headset that is otherwise similar in structure and function to the headset 100 may include curved fixtures that have an over the ear configuration.

Figure 9:
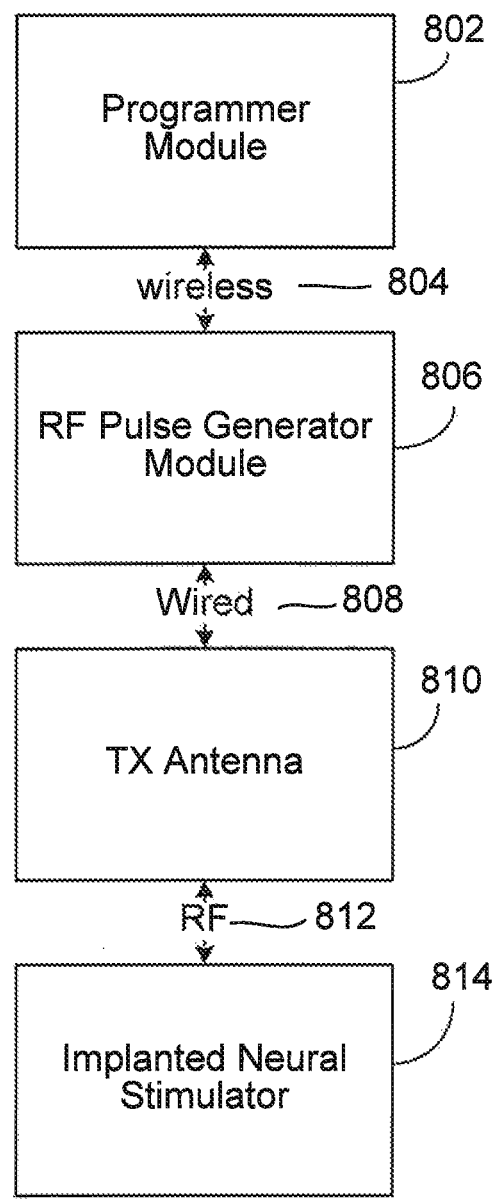
FIG. 9 is a system block diagram of a neural stimulation system including an antenna that can be secured to a head of a patient using the headset of FIG. 1

In some embodiments, the antenna 810 and a tissue stimulator 814 may be provided as part of a tissue stimulation system, such as a neural stimulation system 800. Referring to FIG. 9, the neural stimulation system 800 is designed to send electrical pulses to a nearby (e.g., adjacent or surrounding) target nerve tissue to stimulate the target nerve tissue by using remote radio frequency (RF) energy without cables and without inductive coupling to power the tissue stimulator 814. Accordingly, the tissue stimulator 814 is provided as a passive tissue stimulator in the neural stimulation system 800. In some examples, the target nerve tissue is in the spinal column and may include one or more of the spinothalamic tracts, the dorsal horn, the dorsal root ganglia, the dorsal roots, the dorsal column fibers, and the peripheral nerves bundles leaving the dorsal column or the brainstem. In some examples, the target nerve tissue may include one or more of cranial nerves, abdominal nerves, thoracic nerves, trigeminal ganglia nerves, nerve bundles of the cerebral cortex, deep brain, sensory nerves, and motor nerves.

The neural stimulation system 800 further includes a programmer module 802, an RF pulse generator module 806 (e.g., a controller module), and a transmit (TX) antenna 810. In some embodiments, the programmer module 802 is a computing device (e.g., a smart phone, another mobile computing device, or a stationary computing device) running a software application that supports a wireless connection 804 (e.g., via Bluetooth®). The software application can enable the user to view a system status and system diagnostics, change various parameters, increase and decrease a desired stimulus amplitude of the electrical pulses, and adjust a feedback sensitivity of the RF pulse generator module 806, among other functions.

The RF pulse generator module 806 includes stimulation circuitry, a battery to power generator electronics, and communication electronics that support the wireless connection 804. In some embodiments, the RF pulse generator module 806 is designed to be worn external to the body, and the TX antenna 810 (e.g., located external to the body) is connected to the RF pulse generator module 806 by a wired connection 808. Accordingly, the RF pulse generator module 806 and the TX antenna 810 may be incorporated into a wearable accessory (e.g., a belt or a harness design) or a clothing article such that electric radiative coupling can occur through the skin and underlying tissue to transfer power and/or control parameters to the tissue stimulator 814.

The TX antenna 810 can be coupled directly to tissues within the body to create an electric field that powers the implanted tissue stimulator 814. The TX antenna 810 communicates with the tissue stimulator 814 through an RF interface. For instance, the TX antenna 810 radiates an RF transmission signal that is modulated and encoded by the RF pulse generator module 806. The tissue stimulator 814 includes one or more antennas (e.g., dipole antennas) that can receive and transmit through an RF interface 812. In particular, the coupling mechanism between the TX antenna 810 and the one or more antennas on the tissue stimulator 814 is electrical radiative coupling and not inductive coupling. In other words, the coupling is through an electric field rather than through a magnetic field. Through this electrical radiative coupling, the TX antenna 810 can provide an input signal to the tissue stimulator 814.

In addition to the one or more antennas, the tissue stimulator 814 further includes internal receiver circuit components that can capture the energy carried by the input signal sent from the TX antenna 804 and demodulate the input signal to convert the energy to an electrical waveform. The receiver circuit components can further modify the waveform to create electrical pulses suitable for stimulating the target neural tissue. The tissue stimulator 814 further includes electrodes that can deliver the electrical pulses to the target neural tissue. For example, the circuit components may include wave conditioning circuitry that rectifies the received RF signal (e.g., using a diode rectifier), transforms the RF energy to a low frequency signal suitable for the stimulation of neural tissue, and presents the resulting waveform to an array of the electrodes. In some implementations, the power level of the input signal directly determines an amplitude (e.g., a power, a current, and/or a voltage) of the electrical pulses applied to the target neural tissue by the electrodes. For example, the input signal may include information encoding stimulus waveforms to be applied at the electrodes.

In some implementations, the RF pulse generator module 806 can remotely control stimulus parameters of the electrical pulses applied to the target neural tissue by the electrodes and monitor feedback from the tissue stimulator 814 based on RF signals received from the tissue stimulator 814. For example, a feedback detection algorithm implemented by the RF pulse generator module 806 can monitor data sent wirelessly from the tissue stimulator 814, including information about the energy that the tissue stimulator 814 is receiving from the RF pulse generator 806 and information about the stimulus waveform being delivered to the electrodes. Accordingly, the circuit components internal to the tissue stimulator 814 may also include circuitry for communicating information back to the RF pulse generator module 806 to facilitate the feedback control mechanism. For example, the tissue stimulator 814 may send to the RF pulse generator module 806 a stimulus feedback signal that is indicative of parameters of the electrical pulses, and the RF pulse generator module 806 may employ the stimulus feedback signal to adjust parameters of the signal sent to the tissue stimulator 814.

In order to provide an effective therapy for a given medical condition, the neural stimulation system 800 can be tuned to provide the optimal amount of excitation or inhibition to the nerve fibers by electrical stimulation. A closed loop feedback control method can be used in which the output signals from the tissue stimulator 814 are monitored and used to determine the appropriate level of neural stimulation current for maintaining effective neuronal activation. Alternatively, in some cases, the patient can manually adjust the output signals in an open loop control method.

Figure 10:
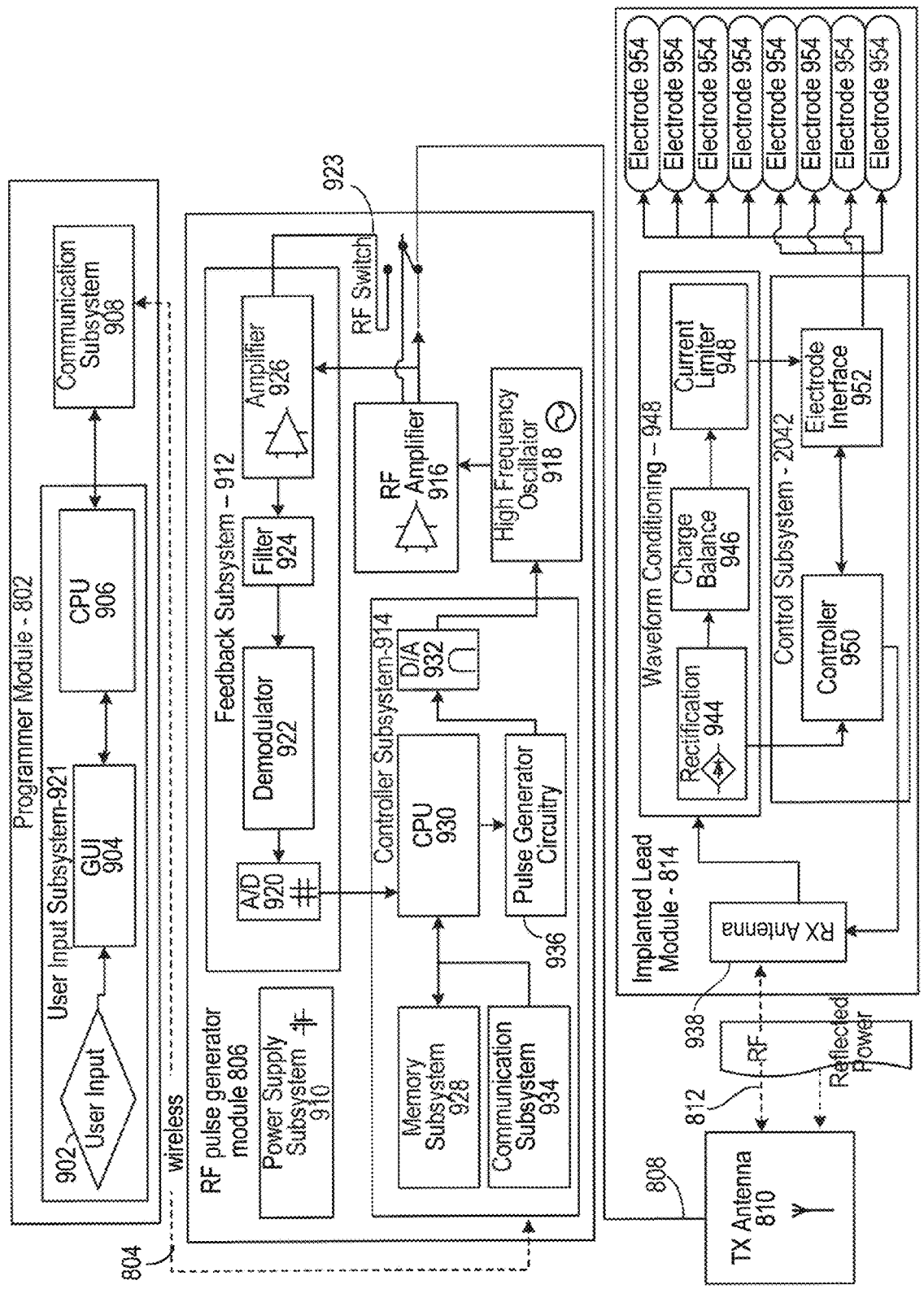
FIG. 10 is a detailed block diagram of the neural stimulation system of FIG. 9.

FIG. 10 depicts a detailed diagram of the neural stimulation system 800. The programmer module 802 may be used as a vehicle to handle touchscreen input on a graphical user interface (GUI) 904 and may include a central processing unit (CPU) 906 for processing and storing data. The programmer module 802 includes a user input system 921 and a communication subsystem 908. The user input system 921 can allow a user to input or adjust instruction sets in order to adjust various parameter settings (e.g., in some cases, in an open loop fashion). The communication subsystem 908 can transmit these instruction sets (e.g., and other information) via the wireless connection 804 (e.g., via a Bluetooth or Wi-Fi connection) to the RF pulse generator module 806. The communication subsystem 908 can also receive data from RF pulse generator module 806.

The programmer module 802 can be utilized by multiple types of users (e.g., patients and others), such that the programmer module 802 may serve as a patient's control unit or a clinician's programmer unit. The programmer module 802 can be used to send stimulation parameters to the RF pulse generator module 806. The stimulation parameters that can be controlled may include a pulse amplitude in a range of 0 mA to 20 mA, a pulse frequency in a range of 0 Hz to 2000 Hz, and a pulse width in a range of 0 ms to 2 ms. In this context, the term pulse refers to the phase of the waveform that directly produces stimulation of the tissue. Parameters of a charge-balancing phase (described below) of the waveform can similarly be controlled. The user can also optionally control an overall duration and a pattern of a treatment.

The tissue stimulator 814 or the RF pulse generator module 806 may be initially programmed to meet specific parameter settings for each individual patient during an initial implantation procedure. Because medical conditions or the body itself can change over time, the ability to readjust the parameter settings may be beneficial to ensure ongoing efficacy of the neural modulation therapy.

Signals sent by the RF pulse generator module 806 to the tissue stimulator 814 may include both power and parameter attributes related to the stimulus waveform, amplitude, pulse width, and frequency. The RF pulse generator module 806 can also function as a wireless receiving unit that receives feedback signals from the tissue stimulator 814. To that end, the RF pulse generator module 806 includes microelectronics or other circuitry to handle the generation of the signals transmitted to the tissue stimulator 814, as well as feedback signals received from tissue stimulator 814. For example, the RF pulse generator module 806 includes a controller subsystem 914, a high-frequency oscillator 918, an RF amplifier 916, an RF switch, and a feedback subsystem 912.

The controller subsystem 914 includes a CPU 930 to handle data processing, a memory subsystem 928 (e.g., a local memory), a communication subsystem 934 to communicate with the programmer module 802 (e.g., including receiving stimulation parameters from the programmer module 802), pulse generator circuitry 936, and digital/analog (D/A) converters 932.

The controller subsystem 914 may be used by the user to control the stimulation parameter settings (e.g., by controlling the parameters of the signal sent from RF pulse generator module 806 to tissue stimulator 814). These parameter settings can affect the power, current level, or shape of the electrical pulses that will be applied by the electrodes. The programming of the stimulation parameters can be performed using the programming module 802 as described above to set a repetition rate, pulse width, amplitude, and waveform that will be transmitted by RF energy to a receive (RX) antenna 938 (e.g., or multiple RX antennas 938) within the tissue stimulator 814. The RX antenna 938 may be a dipole antenna or another type of antenna. A clinician user may have the option of locking and/or hiding certain settings within a programmer interface to limit an ability of a patient user to view or adjust certain parameters since adjustment of certain parameters may require detailed medical knowledge of neurophysiology, neuroanatomy, protocols for neural modulation, and safety limits of electrical stimulation.

The controller subsystem 914 may store received parameter settings in the local memory subsystem 928 until the parameter settings are modified by new input data received from the programmer module 802. The CPU 906 may use the parameters stored in the local memory to control the pulse generator circuitry 936 to generate a stimulus waveform that is modulated by the high frequency oscillator 918 in a range of 300 MHz to 8 GHz. The resulting RF signal may then be amplified by an RF amplifier 926 and sent through an RF switch 923 to the TX antenna 810 to reach the RX antenna 938 through a depth of tissue.

In some implementations, the RF signal sent by the TX antenna 810 may simply be a power transmission signal used by tissue stimulator 814 to generate electric pulses. In other implementations, the RF signal sent by the TX antenna 810 may be a telemetry signal that provides instructions about various operations of the tissue stimulator 814. The telemetry signal may be sent by the modulation of the carrier signal through the skin. The telemetry signal is used to modulate the carrier signal (e.g., a high frequency signal) that is coupled to the antenna 938 and does not interfere with the input received on the same lead to power the tissue stimulator 814. In some embodiments, the telemetry signal and the powering signal are combined into one signal, where the RF telemetry signal is used to modulate the RF powering signal such that the tissue stimulator 814 is powered directly by the received telemetry signal. Separate subsystems in the tissue stimulator 814 harness the power contained in the signal and interpret the data content of the signal.

The RF switch 923 may be a multipurpose device (e.g., a dual directional coupler) that passes the relatively high amplitude, extremely short duration RF pulse to the TX antenna 810 with minimal insertion loss, while simultaneously providing two low-level outputs to the feedback subsystem 912. One output delivers a forward power signal to the feedback subsystem 912, where the forward power signal is an attenuated version of the RF pulse sent to the TX antenna 810, and the other output delivers a reverse power signal to a different port of the feedback subsystem 912, where reverse power is an attenuated version of the reflected RF energy from the TX Antenna 810.

During the on-cycle time (e.g., while an RF signal is being transmitted to tissue stimulator 814), the RF switch 923 is set to send the forward power signal to feedback subsystem 912. During the off-cycle time (e.g., while an RF signal is not being transmitted to the tissue stimulator 814), the RF switch 923 can change to a receiving mode in which the reflected RF energy and/or RF signals from the tissue stimulator 814 are received to be analyzed in the feedback subsystem 912.

The feedback subsystem 912 of the RF pulse generator module 806 may include reception circuitry to receive and extract telemetry or other feedback signals from tissue stimulator 814 and/or reflected RF energy from the signal sent by TX antenna 810. The feedback subsystem 912 may include an amplifier 926, a filter 924, a demodulator 922, and an A/D converter 920. The feedback subsystem 912 receives the forward power signal and converts this high-frequency AC signal to a DC level that can be sampled and sent to the controller subsystem 914. In this way, the characteristics of the generated RF pulse can be compared to a reference signal within the controller subsystem 914. If a disparity (e.g., an error) exists in any parameter, the controller subsystem 914 can adjust the output to the RF pulse generator 806. The nature of the adjustment can be proportional to the computed error. The controller subsystem 914 can incorporate additional inputs and limits on its adjustment scheme, such as the signal amplitude of the reverse power and any predetermined maximum or minimum values for various pulse parameters.

The reverse power signal can be used to detect fault conditions in the RF-power delivery system. In an ideal condition, when TX antenna 810 has perfectly matched impedance to the tissue that it contacts, the electromagnetic waves generated from the RF pulse generator module 806 pass unimpeded from the TX antenna 810 into the body tissue. However, in real-world applications, a large degree of variability exists in the body types of users, types of clothing worn, and positioning of the antenna 810 relative to the body surface. Since the impedance of the antenna 810 depends on the relative permittivity of the underlying tissue and any intervening materials and on an overall separation distance of the antenna 810 from the skin, there can be an impedance mismatch at the interface of the TX antenna 810 with the body surface in any given application. When such a mismatch occurs, the electromagnetic waves sent from the RF pulse generator module 806 are partially reflected at this interface, and this reflected energy propagates backward through the antenna feed.

The dual directional coupler RF switch 923 may prevent the reflected RF energy propagating back into the amplifier 926, and may attenuate this reflected RF signal and send the attenuated signal as the reverse power signal to the feedback subsystem 912. The feedback subsystem 912 can convert this high-frequency AC signal to a DC level that can be sampled and sent to the controller subsystem 914. The controller subsystem 914 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 914 can measure the reflected-power ratio in real time, and according to preset thresholds for this measurement, the controller subsystem 914 can modify the level of RF power generated by the RF pulse generator module 806. For example, for a moderate degree of reflected power the course of action can be for the controller subsystem 914 to increase the amplitude of RF power sent to the TX antenna 810, as would be needed to compensate for slightly non-optimum but acceptable TX antenna coupling to the body. For higher ratios of reflected power, the course of action can be to prevent operation of the RF pulse generator module 806 and set a fault code to indicate that the TX antenna 810 has little or no coupling with the body. This type of reflected power fault condition can also be generated by a poor or broken connection to the TX antenna 810. In either case, it may be desirable to stop RF transmission when the reflected power ratio is above a defined threshold, because internally reflected power can lead to unwanted heating of internal components, and this fault condition means that the system cannot deliver sufficient power to the tissue stimulator 814 and thus cannot deliver therapy to the user.

The controller 942 of the tissue stimulator 814 may transmit informational signals, such as a telemetry signal, through the RX antenna 538 to communicate with the RF pulse generator module 806 during its receive cycle. For example, the telemetry signal from the tissue stimulator 814 may be coupled to the modulated signal on the RX antenna 938, during the on and off state of the transistor circuit to enable or disable a waveform that produces the corresponding RF bursts necessary to transmit to the external (or remotely implanted) pulse generator module 806. The RX antenna 938 may be connected to electrodes 954 in contact with tissue to provide a return path for the transmitted signal. An A/D converter can be used to transfer stored data to a serialized pattern that can be transmitted on the pulse modulated signal from the RX antenna 938 of the tissue stimulator 814.

A telemetry signal from the tissue stimulator 814 may include stimulus parameters, such as the power or the amplitude of the current that is delivered to the tissue from the electrodes 954. The feedback signal can be transmitted to the RF pulse generator module 806 to indicate the strength of the stimulus at the target nerve tissue by means of coupling the signal to the RX antenna 938, which radiates the telemetry signal to the RF pulse generator module 806. The feedback signal can include either or both an analog and digital telemetry pulse modulated carrier signal. Data such as stimulation pulse parameters and measured characteristics of stimulator performance can be stored in an internal memory device within the tissue stimulator 814 and sent on the telemetry signal. The frequency of the carrier signal may be in a range of 300 MHz to 8 GHz.

In the feedback subsystem 912, the telemetry signal can be down modulated using the demodulator 922 and digitized by being processed through the analog to digital (A/D) converter 920. The digital telemetry signal may then be routed to the CPU 930 with embedded code, with the option to reprogram, to translate the signal into a corresponding current measurement in the tissue based on the amplitude of the received signal. The CPU 930 of the controller subsystem 914 can compare the reported stimulus parameters to those held in local memory 928 to verify that the tissue stimulator 814 delivered the specified stimuli to target nerve tissue. For example, if the tissue stimulator 814 reports a lower current than was specified, the power level from the RF pulse generator module 806 can be increased so that the tissue stimulator 814 will have more available power for stimulation. The tissue stimulator 814 can generate telemetry data in real time (e.g., at a rate of 8 kbits per second). All feedback data received from the tissue stimulator 814 can be logged against time and sampled to be stored for retrieval to a remote monitoring system accessible by a health care professional for trending and statistical correlations.

The sequence of remotely programmable RF signals received by the RX antenna 938 may be conditioned into waveforms that are controlled within the tissue stimulator 814 by the control subsystem 942 and routed to the appropriate electrodes 954 that are located in proximity to the target nerve tissue. For instance, the RF signal transmitted from the RF pulse generator module 806 may be received by RX antenna 938 and processed by circuitry, such as waveform conditioning circuitry 940, within the tissue stimulator 814 to be converted into electrical pulses applied to the electrodes 954 through an electrode interface 952. In some implementations, the tissue stimulator 814 includes between two to sixteen electrodes 954.

The waveform conditioning circuitry 940 may include a rectifier 944, which rectifies the signal received by the RX antenna 938. The rectified signal may be fed to the controller 942 for receiving encoded instructions from the RF pulse generator module 806. The rectifier signal may also be fed to a charge balance component 946 that is configured to create one or more electrical pulses such that the one or more electrical pulses result in a substantially zero net charge at the one or more electrodes 954 (that is, the pulses are charge balanced). The charge balanced pulses are passed through the current limiter 948 to the electrode interface 952, which applies the pulses to the electrodes 954 as appropriate.

The current limiter 948 insures the current level of the pulses applied to the electrodes 954 is not above a threshold current level. In some implementations, an amplitude (for example, a current level, a voltage level, or a power level) of the received RF pulse directly determines the amplitude of the stimulus. In this case, it may be particularly beneficial to include current limiter 948 to prevent excessive current or charge being delivered through the electrodes 954, although the current limiter 548 may be used in other implementations where this is not the case. Generally, for a given electrode 954 having several square millimeters of surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the current limiter 948 acts as a charge limiter that limits a characteristic (for example, a current or duration) of the electrical pulses so that the charge per phase remains below a threshold level (typically, a safe-charge limit).

In the event the tissue stimulator 814 receives a "strong" pulse of RF power sufficient to generate a stimulus that would exceed the predetermined safe-charge limit, the current limiter 948 can automatically limit or "clip" the stimulus phase to maintain the total charge of the phase within the safety limit. The current limiter 948 may be a passive current limiting component that cuts the signal to the electrodes 954 once the safe current limit (the threshold current level) is reached. Alternatively, or additionally, the current limiter 948 may communicate with the electrode interface 952 to turn off all electrodes 954 to prevent tissue damaging current levels.

A clipping event may trigger a current limiter feedback control mode. The action of clipping may cause the controller to send a threshold power data signal to the RF pulse generator module 806. The feedback subsystem 912 detects the threshold power signal and demodulates the signal into data that is communicated to the controller subsystem 914. The controller subsystem 914 algorithms may act on this current-limiting condition by specifically reducing the RF power generated by the RF pulse generator module 806, or cutting the power completely. In this way, the RF pulse generator module 806 can reduce the RF power delivered to the body if the tissue stimulator 814 reports that it is receiving excess RF power.

The controller 950 may communicate with the electrode interface 952 to control various aspects of the electrode setup and pulses applied to the electrodes 954. The electrode interface 952 may act as a multiplex and control the polarity and switching of each of the electrodes 954. For instance, in some implementations, the tissue stimulator 814 has multiple electrodes 954 in contact with the target neural tissue, and for a given stimulus, the RF pulse generator module 806 can arbitrarily assign one or more electrodes to act as a stimulating electrode, to act as a return electrode, or to be inactive by communication of assignment sent wirelessly with the parameter instructions, which the controller 950 uses to set electrode interface 952 as appropriate. It may be physiologically advantageous to assign, for example, one or two electrodes 954 as stimulating electrodes and to assign all remaining electrodes 954 as return electrodes.

Also, in some implementations, for a given stimulus pulse, the controller 950 may control the electrode interface 952 to divide the current arbitrarily (or according to instructions from the RF pulse generator module 806) among the designated stimulating electrodes. This control over electrode assignment and current control can be advantageous because in practice the electrodes 954 may be spatially distributed along various neural structures, and through strategic selection of the stimulating electrode location and the proportion of current specified for each location, the aggregate current distribution on the target neural tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes. Furthermore, the frequency of repetition of this stimulus cycle may be synchronous for all of the electrodes 954. However, the controller 950, on its own or in response to instructions from the RF pulse generator module 806, can control electrode interface 952 to designate one or more subsets of electrodes to deliver stimulus waveforms with non-synchronous start and stop times, and the frequency of repetition of each stimulus cycle can be arbitrarily and independently specified.

For example, a tissue stimulator 814 having eight electrodes 954 may be configured to have a subset of five electrodes, called set A, and a subset of three electrodes, called set B. Set A may be configured to use two of its electrodes as stimulating electrodes, with the remainder being return electrodes. Set B may be configured to have just one stimulating electrode. The controller 950 could then specify that set A deliver a stimulus phase with 3 mA current for a duration of 200 us, followed by a 400 us charge-balancing phase. This stimulus cycle could be specified to repeat at a rate of 60 cycles per second. Then, for set B, the controller 950 could specify a stimulus phase with 1 mA current for duration of 500 us, followed by a 800 us charge-balancing phase. The repetition rate for the set B stimulus cycle can be set independently of set A (e.g., at 25 cycles per second). Or, if the controller 950 was configured to match the repetition rate for set B to that of set A, for such a case the controller 950 can specify the relative start times of the stimulus cycles to be coincident in time or to be arbitrarily offset from one another by some delay interval.

In some implementations, the controller 950 can arbitrarily shape the stimulus waveform amplitude, and may do so in response to instructions from the RF pulse generator module 806. The stimulus phase may be delivered by a constant-current source or a constant-voltage source, and this type of control may generate characteristic waveforms that are static. For example, a constant current source generates a characteristic rectangular pulse in which the current waveform has a very steep rise, a constant amplitude for the duration of the stimulus, and then a very steep return to baseline. Alternatively, or additionally, the controller 950 can increase or decrease the level of current at any time during the stimulus phase and/or during the charge-balancing phase. Thus, in some implementations, the controller 950 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the tissue stimulator 814 may include a charge balancing component 946. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units $uC/cm^2$. In order to avoid the irreversible electrochemical reactions such as pH change, electrode dissolution as well as tissue destruction, no net charge should appear at the electrode-electrolyte interface, and it is generally acceptable to have a charge density less than 30 $uC/cm^2$. Biphasic stimulating current pulses ensure that no net charge appears at the electrode 954 after each stimulation cycle and that the electrochemical processes are balanced to prevent net dc currents. The tissue stimulator 814 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode 954 that delivers a negative current with sufficient amplitude to stimulate adjacent neural tissue is called a "stimulating electrode." During the stimulus phase, the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 946 uses one or more blocking capacitors placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitors may be used for each electrode, or a centralized capacitors may be used within the stimulator circuitry prior to the point of electrode selection. The RC network can block direct current (DC). However, the RC network can also prevent low-frequency alternating current (AC) from passing to the tissue. The frequency below which the series RC network essentially blocks signals is commonly referred to as the cutoff frequency, and in some embodiments, the design of the stimulator system may ensure that the cutoff frequency is not above the fundamental frequency of the stimulus waveform. In the example embodiment 800, the tissue stimulator 814 may have a charge-balance capacitor with a value chosen according to the measured series resistance of the electrodes and the tissue environment in which the stimulator is implanted. By selecting a specific capacitance value, the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the tissue stimulator 814 may create a drive-waveform envelope that follows the envelope of the RF pulse received by the RX antenna 938. In this case, the RF pulse generator module 806 can directly control the envelope of the drive waveform within the tissue stimulator 814, and thus no energy storage may be required inside of the tissue stimulator 814, itself. In this implementation, the stimulator circuitry may modify the envelope of the drive waveform or may pass it directly to the charge-balance capacitor and/or electrode-selection stage.

In some implementations, the tissue stimulator 814 may deliver a single-phase drive waveform to the charge balance capacitor or it may deliver multiphase drive waveforms. In the case of a single-phase drive waveform (e.g., a negative-going rectangular pulse), this pulse includes the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the tissue stimulator 814 facilitates the discharge of the charge-balance capacitor. In some implementations, using a passive discharge phase, the capacitor may allow virtually complete discharge prior to the onset of the subsequent stimulus pulse.

In the case of multiphase drive waveforms, the tissue stimulator 814 may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 806, and in other implementations, this control may be administered internally by circuitry onboard the tissue stimulator 814, such as controller 550. In the case of onboard control, the amplitude and timing may be specified or modified by data commands delivered from the pulse generator module 806.

While the RF pulse generator module 806 and the TX antenna 810 have been described and illustrated as separate components, in some embodiments, the RF pulse generator module 806 and the TX antenna 810 may be physically located in the same housing or other packaging. Furthermore, while the RF pulse generator module 806 and the TX antenna 810 have been described and illustrated as located external to the body, in some embodiments, either or both of the RF pulse generator module 806 and the TX antenna 810 may be designed to be implanted subcutaneously. While the RF pulse generator module 806 and the TX antenna 810 have been described and illustrated as coupled via a wired connection 808, in some embodiments (e.g., where the RF pulse generator module 806 is either located externally or implanted subcutaneously), the RF pulse generator module 806 and the TX antenna 810 may be coupled via a wireless connection.

Other embodiments of positioning devices and tissue stimulation systems are within the scope of the following claims.

What is claimed is:

1. A headset for positioning an electronic device against a head of a patient, the headset comprising:
   a frame comprising:
      a first frame portion; and
      an engagement structure coupled to at least one end of the first frame portion, the engagement structure comprising a section configured to extend from under an ear of the patient, wrap around a front edge of the ear, over a top of the ear, and toward a rear of the ear without extending along an entirety of the rear of the ear, to engage the ear of the patient, the frame configured to be placed on the head of the patient in a manner such that the engagement structure is configured to be coupled to the at least one end of the first frame portion in a region below a middle of the ear of the patient; and
   a mount configured to engage the first frame portion and to which the electronic device is attachable.

2. The headset of claim 1, wherein the mount is moveably engaged with the first frame portion to allow a position of the electronic device to be adjusted with respect to the head of the patient.

3. The headset of claim 1, wherein the frame comprises one or more of: acrylonitrile butadiene styrene, rubber, silicone, polyvinyl chloride, and thermoplastics and the mount comprises one or more of: acrylonitrile butadiene styrene, rubber, silicone, polyvinyl chloride, and thermoplastics.

4. The headset of claim 1, wherein the engagement structure has a telescopic arrangement with the first frame portion.

5. The headset of claim 1, wherein a position of the engagement structure relative to the frame is securable via a friction fit.

6. The headset of claim 1, wherein the engagement structure is a first engagement structure, the headset further comprising a second engagement structure configured to engage the other ear of the patient.

7. The headset of claim 1, wherein a position of the mount relative to the frame is securable via a friction fit.

8. The headset of claim 1, wherein the mount is configured to compress the electronic device against the head.

9. The headset of claim 1, wherein the mount is oriented at an angle of about 26.1 degrees to about 26.9 degrees with respect to the frame.

10. The headset of claim 1, wherein the headset has a weight in a range of about 5 g to about 60 g.

11. The headset of claim 1, wherein the first frame portion is configured to be adjacent to a base of the head and at least a back of the head and to extend around the head to couple to the engagement structure at a location in the region below the middle of the ear of the patient.

12. The headset of claim 1, wherein the mount is configured to directly engage the first frame portion.

13. A system comprising:
   an implantable device configured to be implanted in a head of a patient;
   an electronic device configured to communicate with the implantable device; and
   a headset for positioning the electronic device adjacent to the implantable device, the headset comprising:
      a frame comprising:
         a first frame portion; and
         an engagement structure extending from at least one end of the first frame portion, the engagement structure comprising a section configured to extend from under an ear of the patient, wrap around a front edge of the ear, over a top of the ear, and toward a rear of the ear, to engage the ear of the patient, the frame configured to be placed on the head of the patient in a manner such that the engagement structure is configured to extend from the at least one end of the first frame portion in a region below a middle of the ear of the patient; and
      a mount configured to engage the first frame portion and to which the electronic device is attachable.

14. The system of claim 13, wherein the electronic device comprises an antenna that is configured to communicate with the implantable device implanted within the head.

15. The system of claim 13, wherein the mount is moveably engaged with the first frame portion to allow a position of the electronic device to be adjusted with respect to a location of the implantable device in the head of the patient.

16. The system of claim 13, wherein the first frame portion is configured to be adjacent to a location of the implantable device in the head of the patient.

17. The system of claim 13, wherein the mount is configured to directly engage the first frame portion.

18. A headset for positioning an electronic device against a head of a patient, the headset comprising:
   a frame comprising:
      a first frame portion; and
      an engagement structure extending from at least one end of the first frame portion, the engagement structure comprising a section configured to extend from under an ear of the patient, wrap around a front edge of the ear, over a top of the ear, and toward a rear of the ear, to engage the ear of the patient, the frame configured to be placed on the head of the patient in a manner such that the engagement structure is configured to extend from the at least one end of the first frame portion in a region below a middle of the ear of the patient; and
   a mount to which the electronic device is attachable, the mount configured to slide along the first frame portion to allow the position of the electronic device to be adjusted with respect to the head of the patient.

19. The headset of claim 18, wherein the first frame portion is configured to be adjacent to a base of the head.

20. The headset of claim 18, wherein the engagement structure has a telescopic arrangement with the first frame portion.

\* \* \* \* \*